United States Patent
Vanasse et al.

(10) Patent No.: US 8,843,229 B2
(45) Date of Patent: Sep. 23, 2014

(54) METALLIC STRUCTURES HAVING POROUS REGIONS FROM IMAGED BONE AT PRE-DEFINED ANATOMIC LOCATIONS

(75) Inventors: Tom Vanasse, Warsaw, IN (US);
Gautam Gupta, Warsaw, IN (US);
Jason Meridew, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/554,484

(22) Filed: Jul. 20, 2012

(65) Prior Publication Data
US 2014/0025181 A1    Jan. 23, 2014

(51) Int. Cl.
*G06F 19/00* (2011.01)
(52) U.S. Cl.
USPC .............................. 700/98; 600/421; 606/280
(58) Field of Classification Search
USPC ....................... 700/98, 100; 600/421; 606/280
See application file for complete search history.

(56) References Cited

U.S. PATENT DOCUMENTS

| | | | |
|---|---|---|---|
| 5,047,395 A * | 9/1991 | Wu | 514/15.1 |
| 5,639,402 A * | 6/1997 | Barlow et al. | 264/6 |
| 6,283,997 B1 * | 9/2001 | Garg et al. | 623/16.11 |
| 6,730,252 B1 * | 5/2004 | Teoh et al. | 264/178 F |
| 6,993,406 B1 * | 1/2006 | Cesarano et al. | 700/119 |
| 7,174,282 B2 | 2/2007 | Hollister et al. | |
| 7,509,183 B2 | 3/2009 | Lin et al. | |
| 7,537,664 B2 | 5/2009 | O'Neill et al. | |
| 7,758,792 B2 | 7/2010 | Yamazawa et al. | |
| 7,968,026 B1 * | 6/2011 | Teoh et al. | 264/173.12 |
| 2007/0083266 A1 | 4/2007 | Lang | |
| 2007/0118243 A1 | 5/2007 | Schroeder et al. | |
| 2007/0142914 A1 | 6/2007 | Jones et al. | |
| 2007/0276501 A1 | 11/2007 | Betz et al. | |
| 2008/0262624 A1 * | 10/2008 | White et al. | 623/20.32 |
| 2009/0051082 A1 | 2/2009 | Nakamura et al. | |
| 2010/0291401 A1 | 11/2010 | Medina et al. | |
| 2010/0292963 A1 | 11/2010 | Schroeder | |
| 2011/0022174 A1 | 1/2011 | Holdstein et al. | |
| 2013/0264749 A1 | 10/2013 | Jones et al. | |

FOREIGN PATENT DOCUMENTS

WO    WO 2012/154534 A1    11/2012

OTHER PUBLICATIONS

International Search Report and Written Opinion from PCT/US2013/046711, mailed Aug. 23, 2013, 16 pages.
Quadrani, et al, High-resolution 3D scaffold model for engineered tissue fabrication using a rapid prototyping technique. Med. Biol. Eng. and Comp. 43(2): 196-199 (2005).
Sun, W., Starly, B., Nam, J., Darling, A.: Bio-CAD modeling and its applications in computer-aided tissue engineering. Computer-Aided Design 37, 1097-1114 (2005).
Cooper D., Turinsky A, Sensen C, Hallgrimsson B. Effect of voxel size on 3D micro-CT analysis of cortical bone porosity. Calcif Tissue Int. 2007;80(3):211-219.

* cited by examiner

*Primary Examiner* — Kidest Bahta
(74) *Attorney, Agent, or Firm* — Taft Stettinius & Hollister, LLP; Ryan O. White

(57) ABSTRACT

A method of forming an implant having a porous region replicated from scanned bone, the method comprising imaging bone with a high resolution digital scanner to generate a three-dimensional design model of the bone; removing a three-dimensional section from the design model; fabricating a porous region on a digital representation of the implant by replacing a solid portion of the digital implant with the section removed from the digital representation; and using an additive manufacturing technique to create a physical implant including the fabricated porous region.

15 Claims, 6 Drawing Sheets

METALLIC STRUCTURES HAVING POROUS REGIONS FROM IMAGED BONE AT PRE-DEFINED ANATOMIC LOCATIONS

TECHNICAL FIELD

The present invention generally relates to metallic structures having porous or mesh regions that represent the architecture of bone, and specifically to methods for imaging bone at pre-defined anatomic locations to create implants having porous regions that represent the bone's architecture at those imaged anatomic locations.

BACKGROUND OF THE INVENTION

Devices used to replace various joints of the human body are often implanted without the use of bone cement. To achieve and maintain long-term fixation and stability, these implants generally require some degree of bony on-growth or in-growth. The bony on-growth or in-growth necessary to promote and encourage the growth of surrounding bony and soft tissues, as well as to achieve desirable long-term fixation and stability properties, is often enhanced by fabricating porous coatings into one or more surfaces of the implant. Depending on the various features of the fabricated porous coatings (e.g., their pore size and roughness characteristics), the resulting osteoconductive properties of the implant can be improved in such a manner that the porous surfaces are able to function as scaffolds exhibiting desirable load-bearing strengths at the implantation site.

While several orthopedic device companies commercially offer implants having porous surfaces, these products largely fail to adequately replicate the trabecular structure of bone. Additionally, when an implant is designed for a specific anatomic site, its interaction with the bone is limited to the areas immediately surrounding the implantation site. Bone architecture consists of trabeculae that are oriented in certain patterns in order to optimize the bone performance in that anatomic location. Since the magnitude and mode of differential loading to which a bone is subjected is influenced by the bone's anatomic location, by Wolff's law, trabecular struts in bone can also be expected to have anatomically site-specific architectures.

Over the past few years, additive manufacturing and free-form fabrication processes have experienced some significant advances in terms of fabricating articles directly from computer controlled databases. For instance, rapid prototyping techniques allow many articles (e.g., prototype parts and mold dies) to be fabricated more quickly and cost effectively than conventional machining processes that require blocks of material to be specifically machined in accordance with engineering drawings.

Illustrative modern rapid prototyping technologies include laser based additive manufacturing processes such as selective or direct metal laser sintering processes. These processes utilize digital electronic file formats (e.g., STL files) that can be printed into three-dimensional (3D) CAD models, and then utilized by a prototyping machine's software to construct various articles based on the geometric orientation of the 3D model. The constructed articles are produced additively in a layer-wise fashion by dispensing a laser-fusible powder one layer at a time. The powder is fused, re-melted or sintered, by the application of laser energy that is directed in raster-scan fashion to portions of the powder layer corresponding to a cross section of the article. After each layer of the powder is fused, an additional layer of powder is dispensed, and the process repeated, with fused portions or lateral layers fusing so as to fuse portions of previous laid layers until the article is complete.

Additive manufacturing processes allow for highly complex geometries to be created directly (without tooling) from 3D CAD data, thereby permitting the creation of articles exhibiting high resolution surfaces. While these processes have been useful for detailing various surface properties of produced articles, such processes have struggled to replicate surfaces having reduced three-dimensional structural densities. For instance, such processes are unable to adequately replicate articles having randomized porous or partially randomized porous metallic structures, including metal porous structures having interconnected porosity. As such, there is a need for an additive manufacturing process that can replicate articles having reduced three-dimensional structural densities, including porous and partially porous metallic structures.

The present invention is intended to improve upon and resolve some of these known deficiencies of the art.

SUMMARY OF THE INVENTION

In accordance with one aspect of the present invention, a method of forming an implant having a porous region replicated from scanned bone is provided. The method comprises the steps of imaging bone with a high resolution digital scanner to generate a three-dimensional design model of the bone; removing a three-dimensional section from the design model; fabricating a porous region on a digital representation of the implant by replacing a solid portion of the digital implant with the section removed from the digital representation; and using an additive manufacturing technique to create a physical implant including the fabricated porous region.

In accordance with another illustrative embodiment of the present teachings, the method of forming an implant having a porous region replicated from scanned bone comprises the steps of: creating a digital image of the bone with a microCT scanner; removing any defective artifacts from the digital image; converting the digital image to a three-dimensional design model of the bone; removing a three-dimensional section that structurally replicates the architecture of the bone from the design model; printing the removed design model section on a digital representation of the implant; and creating a physical implant from the printed digital representation by using an additive manufacturing technique.

In still further embodiments, the present invention is further directed to medical implants created in accordance with the present teachings. One such illustrative medical implant includes a metallic body having at least one surface replicated from a high resolution scan of bone and configured to promote bony on-growth or in-growth of tissue. The implant is generated, in accordance with certain illustrative embodiments, using an additive manufacturing technique, such as a Direct Metal Laser Sintering (DMLS) process, an Electron Beam Melting (EBM) process, Selective Laser Sintering (SLS), Fused Deposition Modeling (FDM), Stereolithography (SLA), Laminated Object Manufacturing, Powder Bed and Inkjet Head 3D Printing and Plaster-Based 3D Printing (PP).

In accordance with yet other embodiments of the present invention, a method of forming an implant from scanned bone to fill a bone void is provided. In accordance with this illustrative embodiment, the method comprises the steps of: imaging a voided bone region with a high resolution digital scanner to generate a three dimensional design model of the voided bone region; providing a digital representation of a non-voided bone region; removing a three dimensional section of the non-voided bone region, the removed section having a size that substantially matches the size of the voided bone region; and creating a physical implant from the removed three dimensional section of the non-voided bone region by using an additive manufacturing technique, the implant being configured to be installed within the voided bone region.

Other objects and benefits of the invention will become apparent from the following written description along with the accompanying figures.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein.

Figure 1:
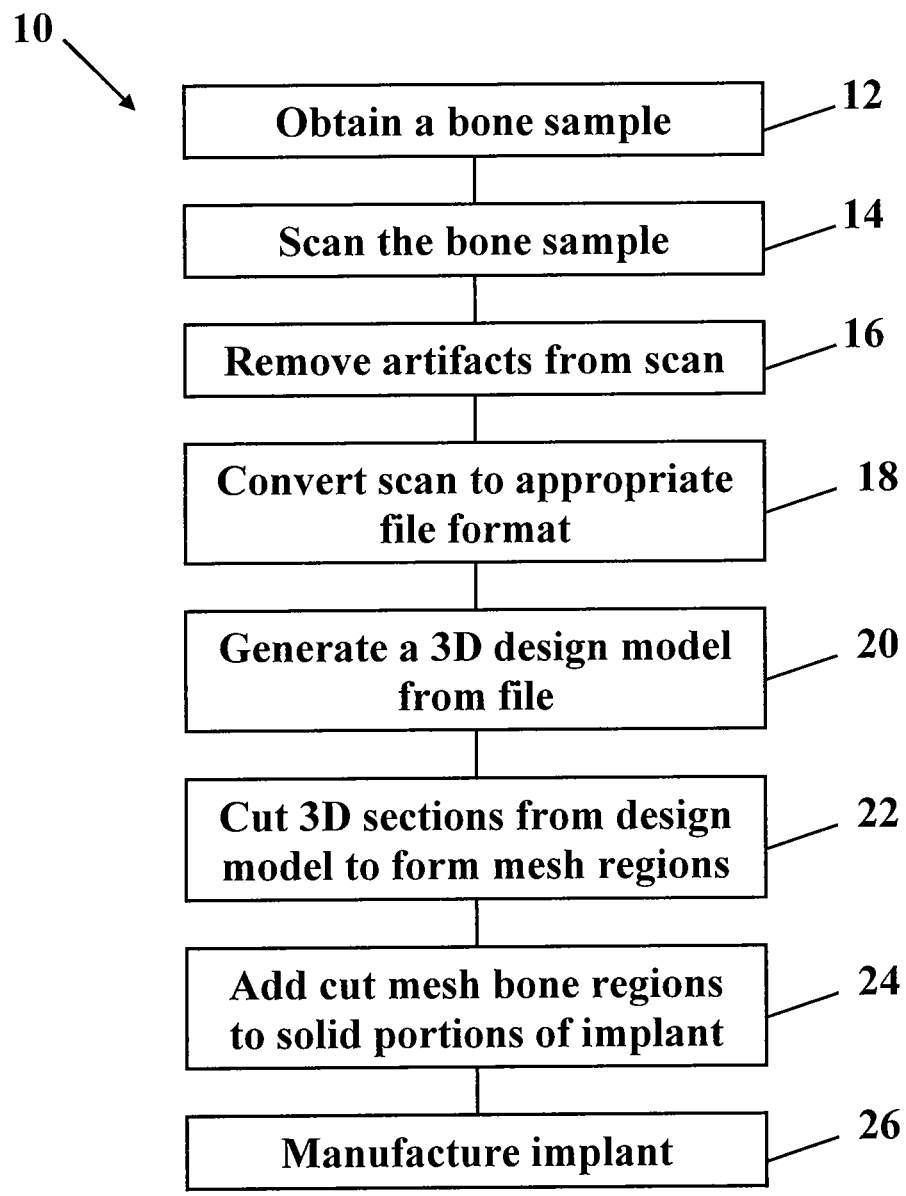
FIG. 1 is a schematic flowchart of an illustrative process for creating a porous region of an implant from a trabecular bone in accordance with the teachings of the present invention.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the disclosed aspects of the invention, as generally described herein, and illustrated in the Figures, may be arranged, substituted, combined, and designed in a wide variety of different configurations, all of which are explicitly contemplated and should be construed as being incorporated into this disclosure.

Unless defined otherwise, all technical and scientific terms used herein have the same meaning as commonly understood by one of ordinary skill in the art to which this invention belongs. Although any method and materials similar or equivalent to those described herein can be used in the practice or testing of the present invention, the specific methods and materials are now described. Moreover, the techniques employed or contemplated herein are standard methodologies well known to one of ordinary skill in the art and the materials, methods and examples are illustrative only and not intended to be limiting.

The present invention relates to methods of forming metallic structures having porous or mesh regions that represent the architecture of bone, and specifically methods for imaging bone at pre-defined anatomic locations to create implants having porous regions that represent the bone's architecture at those imaged anatomic locations. Generally, the methods of the present invention utilize laser technology by employing a variety of scanning strategies. It should be understood and appreciated herein that various different materials can be used to form the metallic structures of the present invention; however, in accordance with certain aspects of the present invention, the metal and metal alloys employed include, but are not limited to, stainless steel, cobalt chromium alloys, titanium and its alloys, tantalum and niobium. It should also be understood and appreciated herein that the present invention can be used for various different medical device applications, including applications in which bone and soft tissue interlock with a component or where a controlled structure is required to more closely match the mechanical properties of the device with surrounding tissue.

In accordance with certain aspects of the present invention, an additive manufacturing process is utilized to create a porous metal structure for an orthopedic device. According to one illustrative embodiment, the porous metal structure is configured to mimic the trabecular architecture of bone at the specific anatomic site where the device is to be implanted. It should be understood and appreciated herein that the teachings of the present invention can be utilized with various different anatomic applications, including, but not limited to, hip procedures, knee procedures, spinal procedures, shoulder procedures, hand, finger, wrist and elbow procedures and foot, toe and ankle procedures.

Moving now to FIG. 1, an illustrative process 10 for creating a porous region of an implant from a trabecular bone is now discussed. In accordance with this illustrative embodiment, a bone sample is first obtained from a region of interest (e.g., humeral head) from a pre-defined and site-specific anatomic site of a specimen (e.g., a cadaver specimen) (step 12). Once the bone sample is obtained from the specimen, the sample is scanned using a high resolution imaging technique (step 14). As those of skill in the art will understand and appreciate, various methods can be employed to quantitatively assess the microstructure of trabecular bone in accordance with the teachings of the present invention. Some of these imaging techniques include, but are not limited to, high-resolution CT (hrCT) and microCT (µCT) techniques and high-resolution magnetic resonance (hrMR) and microMR (µMR) techniques.

Figure 2A:
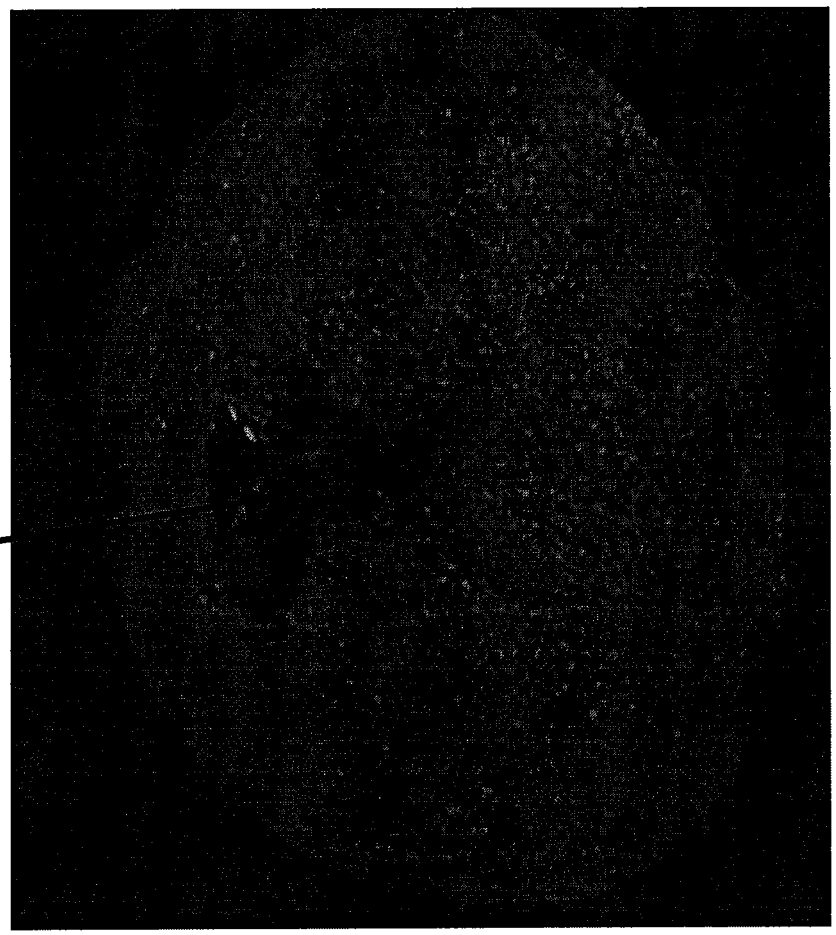
FIGS. 2a and 2b are illustrative MicroCT scans of acetabular bone sections from cadaver pelvises imaged in accordance with the teachings of the present invention.
Figure 2B:
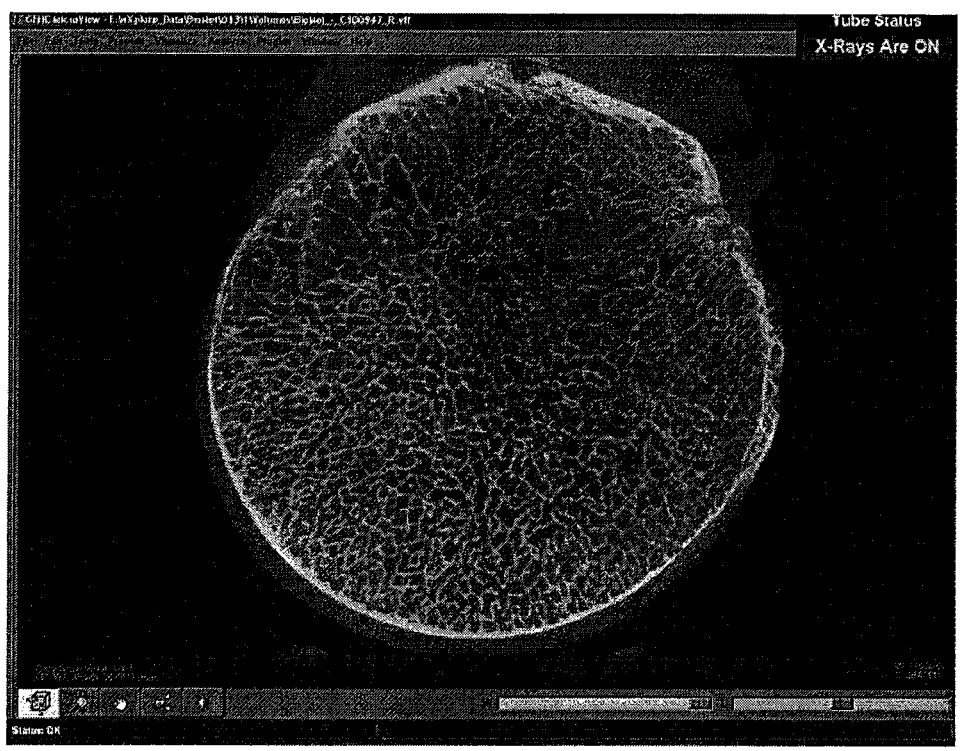

In accordance with specific aspects of the present invention, the obtained bone sample is scanned using a high resolution microCT scanner. For instance, FIGS. 2a and 2b depict acetabular scans obtained from cadaver pelvises using high-resolution microCT scanners. Depending on the selected anatomic site that is used to obtain the bone sample, it is possible that various non-uniformities or discontinuities may exist in the bone structure of the scanned sample. When such artifacts are present in the scanned bone sample image, it may be desirable to clean up or remove these artifacts from the image, thereby leaving only the desired trabecular structure (step 16). For example, as the scanned image of FIG. 2a reveals, the bone in the medial region at the apex has a discontinuity (shown by reference numeral 202), while the remaining regions generally contain a trabecular architecture that is uniform and continuous. While various different known image processing techniques can be used to remove the undesired artifacts from the image (step 16), in accordance with certain aspects of the present invention, bone from regions exhibiting desired trabecular structure can be selected and superimposed to fill in the region or regions containing defects. Alternatively, and in accordance with other embodiments of the present invention, a region of the original bone sample scan containing optimal trabecular architecture can be identified and then used as a unit cell for the entire porous region of the structure to be created.

Once the undesirable artifacts are removed, the scan having the optimal or desired physical properties of the trabecular structure is chosen and the scan converted to a digital file format that is appropriate for printing the porous metal structure using an additive manufacturing process (e.g., STL format, AMF format, etc.) (step 18). In accordance with certain illustrative embodiments of the present teachings, an STL file (i.e., the file format native to the stereolithography CAD software created by 3D Systems) representing the trabecular structure is produced from the microCT scan. In accordance with this specific embodiment, the file can be sliced and the data sent digitally to a scanning control to permit the generation of a layer-by-layer facsimile replica (i.e., a 3D design model) of the scanned sample (step 20).

Once the 3D model is generated, one or more 3D sections of the trabecular structure can be removed or cut from the model to form the desired porous or mesh regions to be fabricated into the implant (step 22). In accordance with certain aspects of the present invention, bone can be selected based on intersection with the model. Moreover, information can be taken from the porous region where the implant would sit in the bone. It should be understood and appreciated herein that the porous or mesh regions of the final metal structures created in accordance with the various embodiments of the present teachings contain the trabecular architecture of natural bone, and as such, the porous structure unit cells do not require the use of a mathematical model to be created. Accordingly, the porous structure of the metallic device created herein will mimic the trabecular architecture of the natural bone from the specific targeted anatomic site.

After the desired mesh regions of the metallic structure are formed, bone sections are then added to the solid portions of the implant model using a software program, such as computer aided design "CAD" software program or the like (step 24). It should be understood and appreciated herein that care should be taken to align the bone sections as they were originally aligned in the native bone when applying the techniques of the present invention as disclosed herein. More particularly, different regions of a bone, such as the humerus, have different trabecular properties (e.g., thickness, length, etc.) and orientation that should be closely replicated in the implant mesh design.

After the implant is modeled, an additive manufacturing process is then employed to manufacture the implant from the 3D model data (step 26). Additive manufacturing processes are generally known in the art and typically involve making objects from 3D model data by joining materials together in a layer-by-layer fashion. Some additive manufacturing processes that can be utilized in accordance with the teachings of the present invention include, but are not limited to, Direct Metal Laser Sintering (DMLS) process, an Electron Beam Melting (EBM) process, Selective Laser Sintering (SLS), Fused Deposition Modeling (FDM), Stereolithography (SLA), Laminated Object Manufacturing, Powder Bed and Inkjet Head 3D Printing, Plaster-Based 3D Printing (PP) and the like.

While not required herein, it should be understood and appreciated that traditional manufacturing techniques (e.g., casting, molding, forming, machining, joining/welding, polishing, blasting, etc.) can also be used in conjunction with the additive manufacturing processes of the present invention if desired. For instance, in accordance with certain aspects of the present invention, it may be desirable to add tapers, grooves and/or threads to the fabricated article. If such additional features are desired, those of skill in the art can incorporate additional manufacturing techniques into the various embodiments of the present teachings without straying from the spirit or scope of the present invention.

In accordance with further aspects of the present teachings, the inventive techniques described herein can be used to form an implant from scanned bone to fill a bone void. In accordance with this illustrative embodiment, a voided bone region is imaged with a high digital scanner (e.g., a microCT scanner) to generate a three dimensional design model of the voided bone region. Once the three dimensional design model of the voided bone region is provided, a digital representation of a non-voided bone region (i.e., a section or sample of bone that does not contain a non-uniformity or void) is provided. As those of skill in the art will understand and appreciate herein, the three dimensional representation of the non-voided bone region can be generated from various different sources, including either an autologous or a non-autologous source. For instance, in accordance with certain aspects of the present invention, the non-voided bone region can be obtained by scanning a good section of the patient's bone— i.e., a section that is devoid of any non-uniformities or discontinuities. Alternatively, in accordance with further illustrative aspects of the present invention, the non-voided bone region can be taken from a computerized database of stock non-voided bone images. As such, it should be understood that the present invention is not intended to be limited herein.

Once the digital representation of the non-voided bone region is provided, a three dimensional section of the non-voided bone region is removed from the image. In accordance with this aspect of the present invention, the removed three dimensional section should have a size that substantially matches the size of the voided bone region. The removed three dimensional section of the scanned non-voided bone is then converted to a file format that is appropriate for printing with an additive manufacturing process (e.g., STL format, AMF format, etc.) (step 18). In accordance with certain illustrative embodiments of the present teachings, an STL file (i.e., the file format native to the stereolithography CAD software created by 3D Systems) representing the removed non-voided bone region is produced from the microCT scan.

The removed three dimensional section of the non-voided bone region is then subjected to an additive manufacturing process so that a physical implant is manufactured from the 3D design model. As explained in detail above, additive manufacturing processes are generally known in the art and typically involve making objects from 3D model data by joining materials together in a layer-by-layer fashion. Some additive manufacturing processes that can be utilized in accordance with the teachings of the present invention include, but are not limited to, Direct Metal Laser Sintering (DMLS) process, an Electron Beam Melting (EBM) process, Selective Laser Sintering (SLS), Fused Deposition Modeling (FDM), Stereolithography (SLA), Laminated Object Manufacturing, Powder Bed and Inkjet Head 3D Printing, Plaster-Based 3D Printing (PP) and the like.

In accordance with this aspect of the present invention, the manufactured physical implant of the non-voided bone region can then be installed within the voided bone region.

Advantages and improvements of the processes, methods and devices of the present invention are demonstrated in the following example. This example is illustrative only and is not intended to limit or preclude other embodiments of the present invention.

EXAMPLE 1

Figure 3:
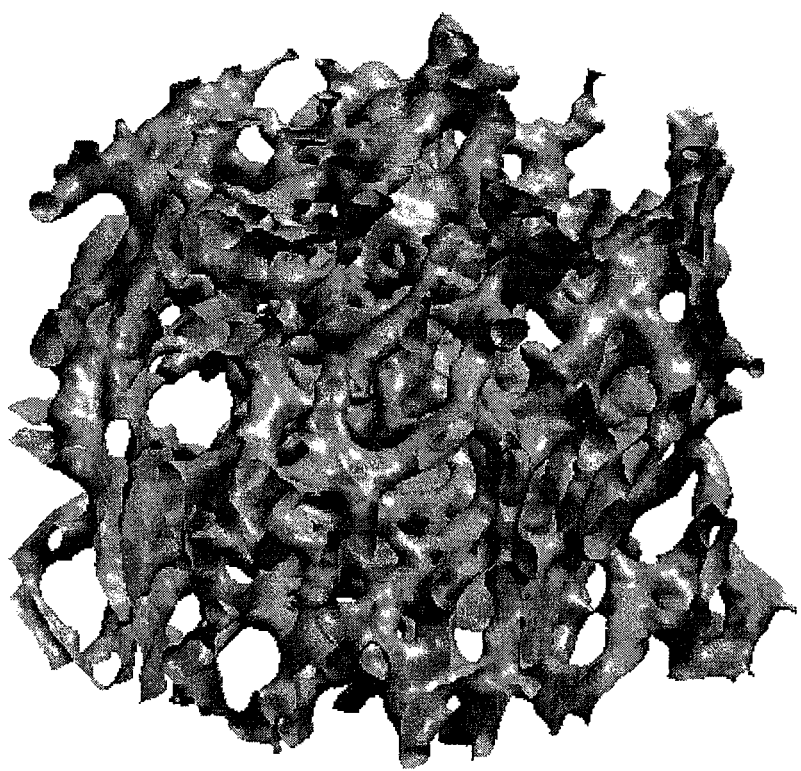
FIG. 3 is an illustrative 3D scan of a trabecular bone obtained from a humeral head in accordance with the techniques of the present invention.

FIG. 3 depicts an illustrative 3D scan of a trabecular bone obtained from a humeral head in accordance with the techniques of the present invention. In accordance with this illustrative embodiment, bone was selected from a cadaver, sectioned, placed in a tube to scan, and then scanned at a resolution of 40 microns. While this scan was taken at a resolution of 40 microns, those of skill in the art will understand and appreciate that various other scanning resolutions can be utilized if desired. For instance in certain illustrative embodiments, a resolution of about 20 microns can be used.

Figure 4:
FIG. 4 is a cross-sectional view of a mesh wing that was created from a humeral head MicroCT scan in accordance with the teachings of the present invention.
Figure 5:
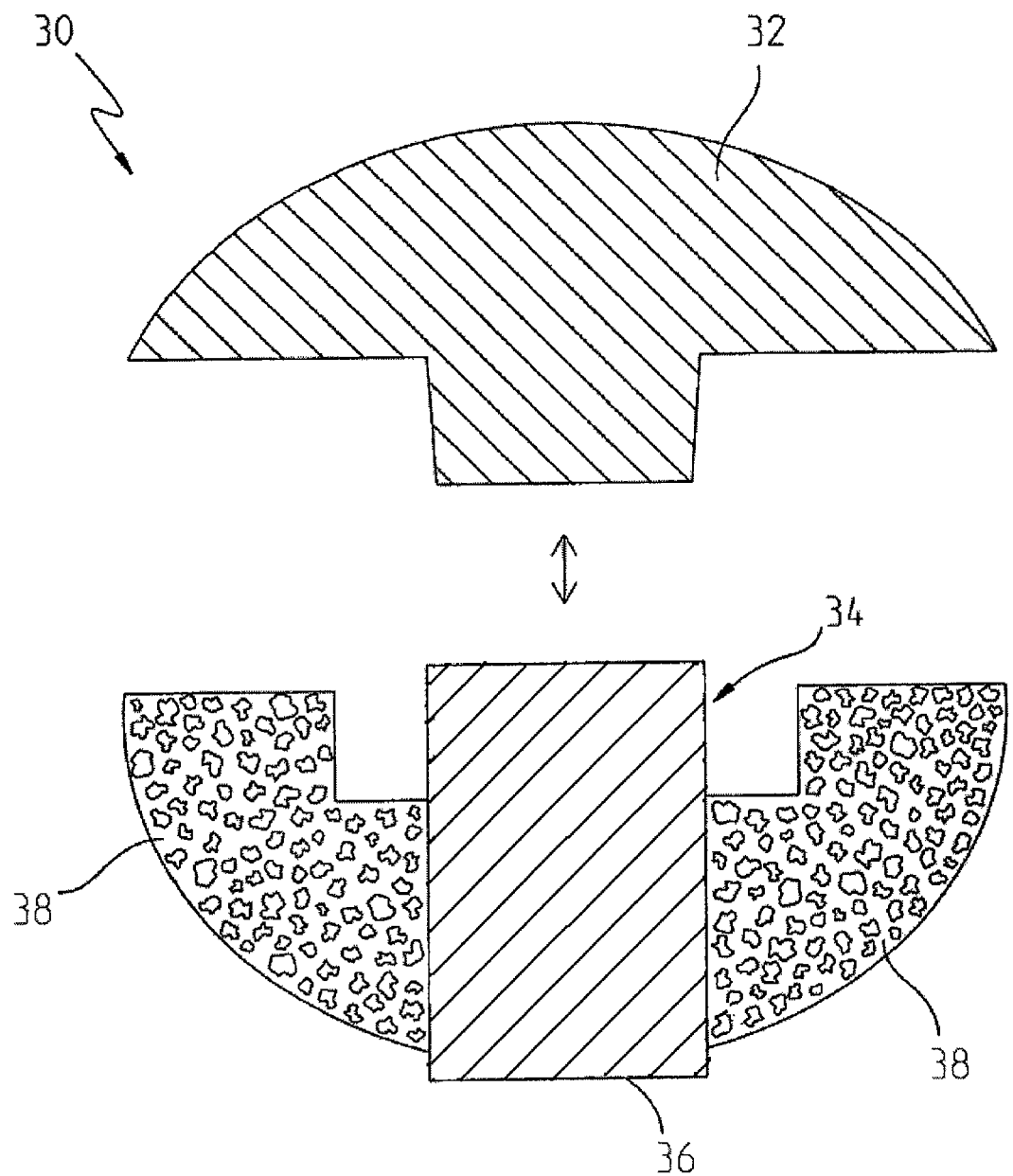
FIG. 5 is a front, cross-sectional view of a stemless shoulder prosthesis having a pair of mesh wings in accordance with the teachings of the present invention.

FIG. 4 shows cross-sectional view of a mesh wing that was created from a humeral head MicroCT scan in accordance with the teachings of the present invention, while FIG. 5 shows a front, cross-sectional view of a stemless shoulder prosthesis 30 having a pair of illustrative mesh wings 38 (such as the mesh wing shown in FIG. 4) coupled thereto. More specifically, and with particular reference to FIG. 5, a humeral head component 32 is configured to be fitted inside a top portion of an internal chamber 34 of the body 36 of the prosthesis. The wings 38 are connected to the body 36 and can be partially or fully porous, as well as have a partial solid section for increased strength if desired. It should be understood and appreciated herein that fully porous wings would allow bone to grow completely through the wings, thereby enhancing the stability of the device. It should also be understood and appreciated herein that in accordance with certain aspects of the present invention, it may be desirable to utilize a biological surface coating (e.g., a titanium porous plasma spray (PPS®) surface coating or a biomimetic coating (e.g., BoneMaster® coating), both of which are commercially available from Biomet), with the porous or nonporous surfaces to create a barrier to particulate debris (metallic, polyethylene or PMMA) and/or to further promote and increase the fixation or osseintegration of the bony in-growth through the wings. In accordance with certain aspects of the present invention, the biological surface coating can have its associated biological performance further enhanced and modified if the coating is subjected to one or more of the following: grit blasting, hyaluronic acid (HA), an RGD-containing glycoprotein or bend coating.

While this illustrative example shows the present teachings utilized with stemless shoulder prosthesis, it should be understood and appreciated herein that the present invention can be incorporated into any implant design that utilizes a porous or mesh structure for bony on-growth or in-growth.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of forming an implant having a porous region replicated from scanned bone, the method comprising the steps of:

imaging bone with a high resolution digital scanner to generate a three-dimensional design model of the bone;

removing a three-dimensional section from the design model;

fabricating a porous region on a digital representation of the implant by replacing a solid portion of the digital implant with the section removed from the design model; and using an additive manufacturing technique to create a physical implant including the fabricated porous region.

2. The method of claim 1, wherein the step of imaging the bone with a high resolution digital scanner comprises scanning the bone with a computed tomography (CT) scanner.

3. The method of claim 2, wherein the step of scanning the bone with a computed tomography (CT) scanner comprises scanning the bone with a MicroCT scanner.

4. The method of claim 1, further comprising modifying any artifacts from the three-dimensional design model of the bone.

5. The method of claim 4, wherein the step of modifying any artifacts from the three-dimensional design model comprises removing defective regions of the design model containing non-uniformities or discontinuities by filling the defective regions with a selected and superimposed region of the bone model that does not contain a non-uniformity or a discontinuity.

6. The method of claim 1, further comprising converting the imaged bone to a digital file format.

7. The method of claim 1, wherein the step of fabricating a porous region on a digital representation of the implant comprises utilizing a computer aided design (CAD) program to fabricate a porous region that structurally replicates the architecture of the bone, the porous region being selected from one of a hip, shoulder, knee, spine, elbow, wrist, ankle, finger and toe.

8. The method of claim 1, wherein the step of using an additive manufacturing technique to create a physical implant comprises using a Direct Metal Laser Sintering (DMLS) process or an Electron Beam Melting (EBM) process, Selective Laser Sintering (SLS), Fused Deposition Modeling (FDM), Stereolithography (SLA), Laminated Object Manufacturing, Powder Bed and Inkjet Head 3D Printing and Plaster-Based 3D Printing (PP).

9. The method of claim 1, further comprising performing an additional manufacturing process on the physical implant to modify one or more features, the manufacturing process being selected from at least one of casting, molding, forming, machining, joining, polishing, blasting and welding.

10. A method of forming an implant having a porous region replicated from scanned bone, the method comprising the steps of:

creating a digital image of the bone with a microCT scanner;

removing any defective artifacts from the digital image;

converting the digital image to a three-dimensional design model of the bone;

removing a three-dimensional section that structurally replicates the architecture of the bone from the design model;

printing the removed design model section on a digital representation of the implant; and creating a physical implant from the printed digital representation by using an additive manufacturing technique.

11. The method of claim 10, wherein the step of printing the removed design model section on a digital representation of the implant comprises using a computer aided design (CAD) program to print the removed design model section.

12. The method of claim 10, wherein the step of removing any defective artifacts comprises removing any defective regions containing a non-uniformity or discontinuity from the image by filling the defective regions with a selected and superimposed region of the digital image that does not contain a non-uniformity or a discontinuity.

13. The method of claim 10, wherein the step of creating a physical implant from the printed digital representation by using an additive manufacturing technique comprises using a Direct Metal Laser Sintering (DMLS) process or an Electron Beam Melting (EBM) process, Selective Laser Sintering (SLS), Fused Deposition Modeling (FDM), Stereolithography (SLA), Laminated Object Manufacturing, Powder Bed and Inkjet Head 3D Printing and Plaster-Based 3D Printing (PP).

14. The method of claim 10, further comprising performing an additional manufacturing process on the physical implant to add one or more features, the manufacturing process being selected from at least one of casting, molding, forming, machining, joining, polishing, blasting and welding.

15. A method of forming an implant from scanned bone to fill a bone void, the method comprising the steps of:

imaging a voided bone region with a high resolution digital scanner to generate a three dimensional design model of the voided bone region;

providing a digital representation of a non-voided bone region;

removing a three dimensional section of the non-voided bone region, the removed section having a size that substantially matches the size of the voided bone region; and creating a physical implant from the removed three dimensional section of the non-voided bone region by using an additive manufacturing technique, the implant being configured to be installed within the voided bone region.

* * * * *